United States Patent
Lange et al.

(10) Patent No.: US 7,406,854 B2
(45) Date of Patent: Aug. 5, 2008

(54) GAS SENSOR

(75) Inventors: Björn Lange, Teschow (DE); Nils Haack, Lübeck (DE); Lars Wulf, Sereetz (DE); Rigobert Chrzan, Bad Oldesloe (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 243 days.

(21) Appl. No.: 11/244,120

(22) Filed: Oct. 5, 2005

(65) Prior Publication Data

US 2006/0162426 A1 Jul. 27, 2006

(30) Foreign Application Priority Data

Jan. 22, 2005 (DE) .................. 10 2005 003 050

(51) Int. Cl.
*G01N 21/00* (2006.01)
*G01N 33/22* (2006.01)

(52) U.S. Cl. .............................. 73/1.06; 73/23.31

(58) Field of Classification Search .............. 73/31.05, 73/23.2, 23.31, 1.04; 422/94; 356/437
See application file for complete search history.

(56) References Cited

U.S. PATENT DOCUMENTS

| | | | |
|---|---|---|---|
| 4,489,590 A * | 12/1984 | Hadden | 73/1.04 |
| 4,709,150 A | 11/1987 | Burough et al. | |
| 4,737,343 A | 4/1988 | Hirschfeld | |
| 4,742,708 A | 5/1988 | Porter | |
| 4,745,796 A * | 5/1988 | Abdelrahman et al. | 73/31.07 |
| 5,326,531 A * | 7/1994 | Hahn et al. | 422/82.06 |
| 5,331,310 A * | 7/1994 | Stetter et al. | 340/632 |
| 5,830,337 A * | 11/1998 | Xu | 204/400 |
| 6,098,523 A * | 8/2000 | Warburton | 73/1.03 |
| 6,165,336 A * | 12/2000 | Maki et al. | 204/415 |
| 6,248,224 B1 * | 6/2001 | Kitzelmann | 204/431 |
| 6,346,179 B1 * | 2/2002 | Makino et al. | 204/428 |
| 6,358,384 B1 * | 3/2002 | Warburton | 204/427 |
| 6,370,941 B2 * | 4/2002 | Nakamura et al. | 73/31.05 |
| 6,453,723 B1 * | 9/2002 | Ichikawa et al. | 73/23.2 |
| 6,469,303 B1 * | 10/2002 | Sun et al. | 250/343 |
| 6,695,959 B2 * | 2/2004 | Kiesele | 204/415 |
| 2001/0011475 A1 * | 8/2001 | Nakamura et al. | 73/31.05 |
| 2003/0159930 A1 * | 8/2003 | Kiesele | 204/415 |
| 2004/0079637 A1 * | 4/2004 | Maeno et al. | 204/431 |
| 2004/0093930 A1 | 5/2004 | Matsunami et al. | |
| 2005/0230624 A1 | 10/2005 | Schubert | |

FOREIGN PATENT DOCUMENTS

| | | |
|---|---|---|
| DE | 10204458 A1 * | 8/2003 |
| EP | 1 063 519 A1 | 12/2000 |

(Continued)

*Primary Examiner*—Hezron E. Williams
*Assistant Examiner*—John Fitzgerald
(74) *Attorney, Agent, or Firm*—McGlew & Tuttle, P.C.

(57) ABSTRACT

A gas sensor is provided that is delimited from the environment with a preferably replaceable cap (8) made of a porous, gas-permeable and water-impermeable material, especially sintered PTFE. The gas sensor is protected against environmental moisture and can be permanently provided with the cap (8) and with a special calibrating adapter (9) both during the gas measurement and during the necessary calibration. Due to the special design of the cap (8) and the calibrating adapter (9), the gas sensor offers the possibility of remote calibration, which can be carried out with high accuracy and is independent from weather effects, especially wind.

17 Claims, 2 Drawing Sheets

FOREIGN PATENT DOCUMENTS

| | | |
|---|---|---|
| EP | 1 106 999 A2 | 6/2001 |
| EP | 1 452 853 A1 | 9/2004 |
| EP | 0 100 667 B1 | 10/2007 |
| GB | 2 101 310 | 1/1983 |
| GB | 22 62 338 | 6/1993 |
| JP | 2002 131 268 | 5/2002 |
| JP | 2003227794 | 8/2003 |
| WO | WO 02/04926 | 1/2002 |
| WO | WO 03/060500 | 7/2003 |
| WO | WO 03/067241 | 8/2003 |
| WO | WO 03/095990 | 11/2003 |

\* cited by examiner

GAS SENSOR

CROSS REFERENCE TO RELATED APPLICATIONS

This application claims the benefit of priority under 35 U.S.C. § 119 of German Patent Application 10 2005 003 050.5 filed Jan. 22, 2005, the entire contents of which are incorporated herein by reference.

FIELD OF THE INVENTION

The present invention pertains to a gas sensor with a measuring element, which generates a measured signal that depends on the concentration of the measured gas.

BACKGROUND OF THE INVENTION

Examples of such gas sensors are infrared optical and electrochemical gas sensors as well as catalytic heat tone sensors. Within their housings, these gas sensors have a measuring cell, in which the gases to be measured are detected on the basis of physical or chemical processes. Depending on the conditions of use, regular calibration with a calibrating gas of known concentration is to be performed for the operation of such gas sensors. According to the current state of the art, this is carried out, as a rule, by pulling a calibrating adapter, which is flushed with a known calibrating gas, for example, from a pressurized gas cylinder, over the gas sensor for each calibration. To be independent from the wind in the measuring environment during the calibration, the calibrating adapter is gas-tight to the calibrating gas, except for the connection of the gas cylinder and a small opening for the discharge of the gas.

Such a prior-art calibrating adapter for an electrochemical gas sensor is described, for example, in U.S. Pat. No. 4,742,708. One drawback of the prior-art calibrating adapter is that free diffusion of the gas to the measuring cell is prevented by the calibrating adapter itself, so that the calibrating adapter is placed on the gas sensor for the duration of the calibration only and must subsequently be removed in an additional operation. This is associated with manual effort and consequently costs especially in case of stationarily installed gas sensors at poorly accessible measuring sites or under difficult environmental conditions involving exposure to wind or health hazard.

SUMMARY OF THE INVENTION

Thus, the object of the present invention is to provide a gas sensor with a special calibrating adapter, which calibrating adapter remains connected with the gas sensor during the calibration and during the measurement.

According to the invention, a gas sensor is provided with a measuring element, which generates a measured signal that depends on the concentration of the measured gas, wherein the gas sensor is delimited from the environment with a cap made of a porous, gas-permeable and water-impermeable material.

A calibrating adapter, which has a gas admission pipe connection for supplying the calibrating gas to the cap of the gas sensor, may be attached to or screwed on the cap. The cap and the calibrating adapter may be designed such that they can be replaced individually or together. The cap and the calibrating adapter may also be designed as a one-piece component.

The cap may advantageously consist essentially of PTFE (polytetrafluoroethylene) or hydrophobized PE (polyethylene), especially a sintered PTFE or sintered hydrophobized PE with a pore volume of about 30% to 70%. The cap may advantageously be white.

The gas sensor may be an infrared optical gas sensor and the measuring element may be an infrared detector. The gas sensor may be an electrochemical gas sensor and the measuring element may be a measuring electrode. The gas sensor may be a catalytic heat tone sensor and the measuring element may be a pellistor.

A porous, sintered metal body may be arranged as an explosion protection means between the measuring element and the cap.

The cap may have a smaller layer thickness and/or a higher porosity in the area of the gas admission pipe connection than in the rest of the area. The gas sensor may be equipped with a cuvette heater in the area of the gas admission pipe connection of the calibrating adapter. The cap and the calibrating adapter may be connected to the gas sensor both during the use for measurement and during the calibration. The flow resistance of the material of the cap may be selected to be such that the pressure in the measuring cell exceeds the dynamic pressure of the wind on the outer side of the cap with the calibrating adapter during the calibration by means of calibrating gas fed in. Due to the geometry of the calibrating adapter and the flow resistance of the material of the cap, the diffusion of measured gas to the measuring element may be hindered only to the extent that the response time of the gas sensor during the gas measurement is prolonged by less than 30% compared to the operation without calibrating adapter and cap. The flow resistance of the material of the cap may be selected to be such that the overpressure generated in the measuring cell by the calibrating gas flow through the gas admission pipe connection does not exceed 50 hPa.

Due to the use of a cap made of a porous, gas-permeable and water-impermeable material for delimiting the gas sensor from the environment according to the principal claim, it is achieved that the diffusion of gas from the environment into the measuring cell is hindered to a very limited extent only, so that the cap can also remain mounted on the gas sensor during the measuring operation, as a consequence of which the maintenance effort is substantially reduced.

According to a preferred embodiment, the porous cap consists of PTFE (polytetrafluoroethylene) or hydrophobized PE (polyethylene), especially a sintered PTFE or sintered hydrophobized PE with a pore volume of about 30% to 70%, and the material of the cap is selected according to another, especially preferred embodiment such that the overpressure of the calibrating gas in the gas sensor in the area of the measuring cell exceeds the dynamic pressure of the wind on the outer side of the cap with the calibrating adapter, but is at most 50 hPa. Complete flushing of the measuring cell in the gas sensor can thus be achieved. Calibration and measurement are also made possible at high wind speed in the environment of the gas sensor and in case of wet weather, and the calibration error due to increased pressure of the calibrating gases in the area of the measuring cell are limited.

According to another preferred embodiment, the cap and the calibrating adapter are permanently connected to the gas sensor both during the use for measurement and during the calibration, so that the maintenance and calibration effort is considerably reduced with a permanently installed calibrating gas feed line especially in case of gas sensors installed at poorly accessible sites.

The invention provides an improved gas sensor, which is better protected against harsh environmental conditions and at the same time creates the precondition, due to the safety device used, of continuing to be provided with a special calibrating adapter during the calibration with a calibrating gas as well, so that the measuring and maintenance effort required for the measurement and the calibration at the gas sensor is substantially reduced.

An exemplary embodiment of the present invention will be explained below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
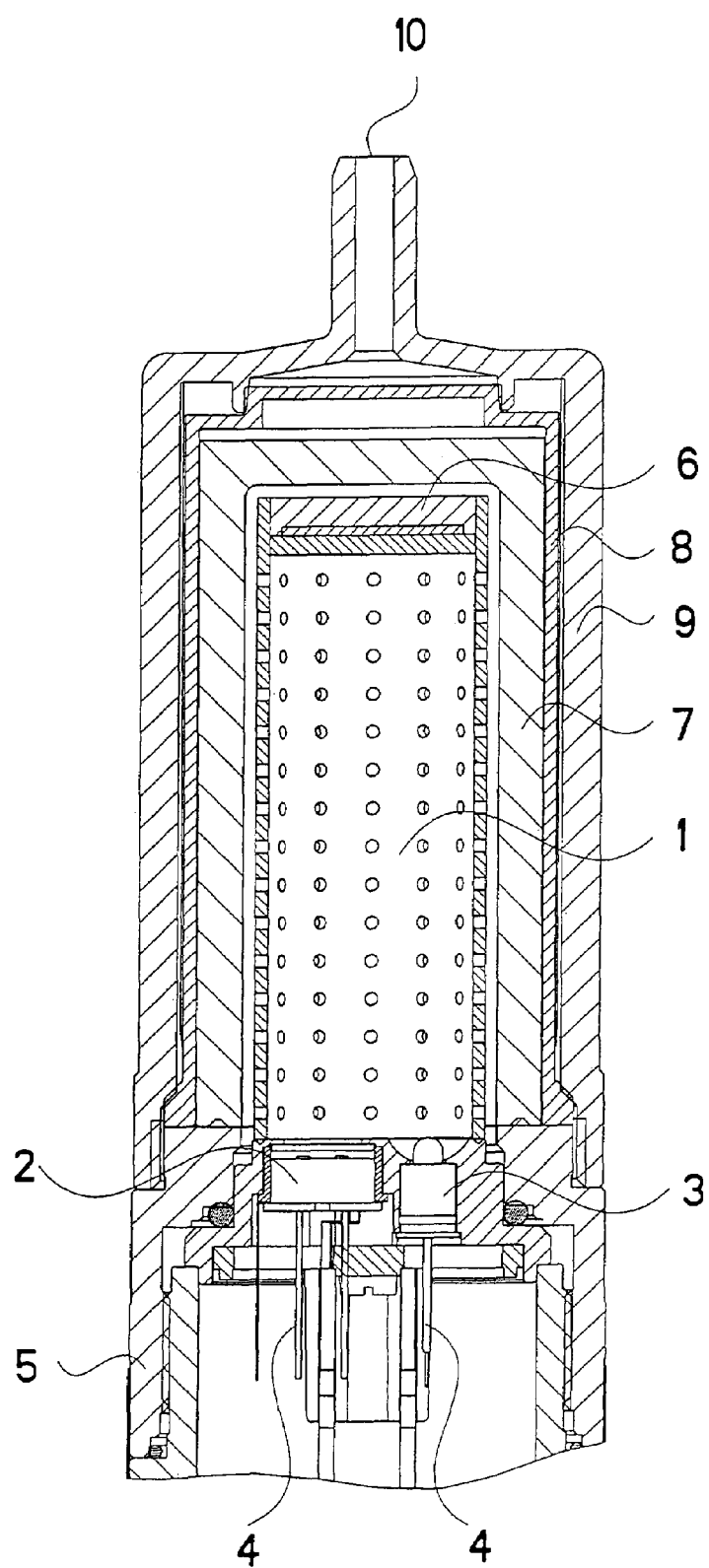
FIG. 1 is a sectional view through an infrared optical gas sensor according to the invention.

Referring to the drawings in particular, the gas sensor in FIG. 1 is an infrared optical gas sensor with a radiation source 3 and with a measuring element 2 designed as an infrared detector, both of which are arranged in the base area 5 of the gas sensor, which said base area is made of metal or even a plastic. The electric contacts 4 are connected to an electronic evaluating unit of the gas sensor, which joins the base area 5. The cylindrical measuring gas cuvette 1 has a radiation-reflecting design on the inside in case of the infrared optical gas sensor and has perforations, which are distributed over the jacket surface and make possible the diffusion of the gas, whose concentration is to be measured, into the cuvette. Such a gas sensor is, for example, a stationary gas sensor installed at a certain measuring site, which may be poorly accessible, as it is used, for example, in industrial or process plants in the chemical or petroleum/natural gas industry. Especially in case of an explosion-proof design, a cylindrical, porous, sintered metal body 7 is rigidly connected as an explosion protection means with the base area 5 in the gas sensor being shown, so hat no explosion of the possibly explosive gases present in the environment can be triggered by electric sparks in the gas sensor. Moisture effects and errors of measurement due to condensation in the gas sensor are to be prevented from occurring with the electric heater 6.

Figure 2:
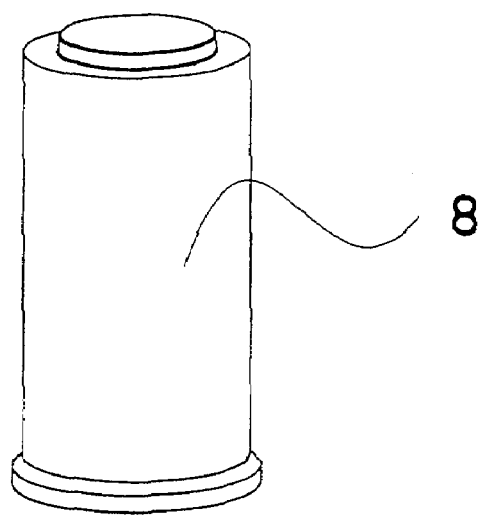
FIG. 2 is a perspective view of a cap from the gas sensor according to FIG. 1.

A preferably replaceable, likewise cylindrical cap 8 made of a porous, gas-permeable and water-impermeable material is attached to or screwed on the porous, sintered metal body 7, cf. FIG. 2. The cap 8 is preferably manufactured from a light-colored to white, porous, sintered PTFE or porous, sintered hydrophobized PE (polyethylene) with a pore volume of about 30% to 70% and with a layer thickness of, e.g., about one mm. Due to the light color of the material of the cap 8, the state of consumption will be readily visible for a possible replacement after corresponding exposure to dust or environmental effects. The porous hydrophobic material of the cap 8, especially PTFE or hydrophobized PE, ensures that no moisture will penetrate into the gas sensor or the metal body 7 and it will not consequently damage these and compromise their measuring function.

Figure 3:
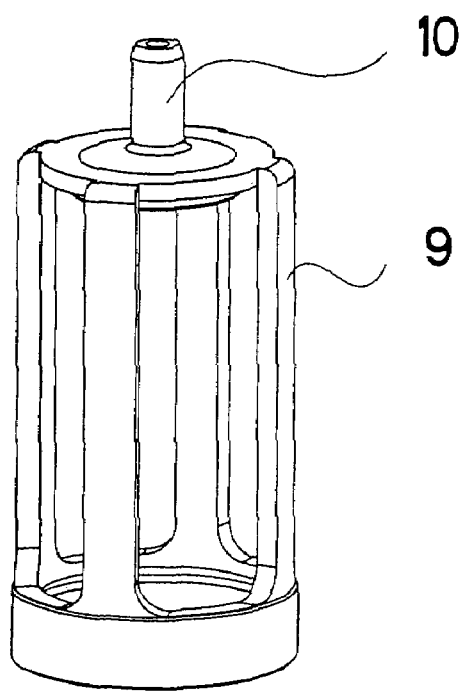
FIG. 3 is a perspective view of a calibrating adapter from a gas sensor according to FIG. 1.

A calibrating adapter 9, see FIG. 3, which is screwed on the gas sensor and is manufactured, for example, from a glass fiber-reinforced plastic such as polyacryl, is located above the metal body 7 with the cap 8. The calibrating adapter 9 is manufactured with perforations or slots (openings) in order to hinder the diffusion of the gas from the environment through the surface of the cap 8 as little as possible and it has, at the upper end, a gas admission pipe connection 10 for connecting a feed line for a calibrating gas from a pressurized gas storage unit, for example, from a pressurized calibrating gas cylinder.

The calibrating adapter 9 preferably remains on the gas sensor both during the measurement and during the calibration, so that if the calibrating gas storage unit is connected to the gas admission pipe connection 10, remote calibration is readily possible, if needed, by opening the calibrating gas storage unit, at any rate without an assembly being needed, as before, for the changeover. This is especially advantageous in case of poorly accessible measuring sites.

The flow resistance of the porous material of the cap 8 is selected by selecting the layer thickness and/or the porosity such that the pressure in the inner area, i.e., in the area of the measuring cell, exceeds the dynamic pressure of the wind on the outer side of the cap 8 with the calibrating adapter 9 attached during the calibration by means of calibrating gas supplied via the gas admission pipe connection 10, so that the calibration is not affected by wind. The cap 8 is preferably made with a smaller layer thickness and/or with a higher porosity in the area of the gas admission pipe connection 10 than in the rest of the area in order to make it possible for the calibrating gas to enter the interior space of the cap 8 and of the measuring cell as unhindered as possible, so that the lowest possible calibrating gas pressure is necessary. In the area of the gas admission pipe connection 10 in the upper section of the cap 8, the calibrating adapter 9 is designed; for example, in the form of a base section such that good sealing of the area in which the calibrating gas flows into the cap 8 is ensured. The rest of the area of the cap 8 is selected to be such that in case of a calibrating gas flow of, e.g., 1 L/minute, an overpressure is generated in the measuring cell, which at least corresponds to the dynamic pressure of the maximum tolerable external wind speed during the calibration operation, so that the calibration is not affected in an unacceptable manner. On the other hand, the inflow of the gas to be measured through the cap 8 must be as unhindered as possible during the rest of the measurement time with the calibrating adapter 9 screwed on. The pressure build-up at the material of the cap 8, through which material the flow takes place, is proportional to the calibrating gas flow, but inversely proportional to the conductance of the air and the size of the area through which the flow takes place. It was determined that in case of acceptable calibrating gas flows of about 1 L/minute with a residual effective surface totaling about 45 cm$^2$ outside of the area in which the calibrating gas flows in, the conductance L of the air equals $$L = \frac{\text{calibrating gas flow}}{\text{area flown through} \cdot \text{pressure build-up}}$$

$$= \frac{1 L/\text{minute}}{45 \text{ cm}^2 \cdot 4 hPa} \approx \frac{100 \text{ mL}}{s \cdot \text{cm}^2 \cdot \text{bar}}$$

at the desired pressure build-up of 4 hPa corresponding to the dynamic pressure in case of a wind speed of 26 m/sec.

If a pressure build-up of 50 hPa corresponding to an approximately 5% increase compared to the atmospheric pressure is desired with the same cap geometry (45 cm$^2$ effective flown-through surface) in order to achieve insensitivity to higher wind speeds of up to 90 m/sec, it would be necessary to select a lower conductance of the air, equaling $$L \approx \frac{7.5 \text{ mL}}{s \cdot \text{cm}^2 \cdot \text{bar}}.$$

However, a correspondingly increased response time of the gas sensor would also have to be accepted in this case during diffusion measurement operation.

While a specific embodiment of the invention has been shown and described in detail to illustrate the application of the principles of the invention, it will be understood that the invention may be embodied otherwise without departing from such principles.

What is claimed is:

1. A gas sensor, comprising:
   a measuring element, which generates a measured signal that depends on the concentration of a measured gas;
   a cylindrical cap to delimit the gas sensor from the environment, said cylindrical cap having a top wall and a side wall made of a porous, gas-permeable and water-impermeable material, whereby gas passes through said top wall in an axial direction and gas passes through said side wall in a radial direction, said top wall and said side wall having a surface exposed to the environment; and
   a calibrating adapter having a gas admission pipe connection for supplying a calibrating gas to the cap of the gas sensor, said calibrating adapter being attached to or screwed on the cap, said cap having a smaller layer thickness and/or a higher porosity in an area of the gas admission pipe connection than in a remaining area.

2. A gas sensor in accordance with claim 1, wherein the cap and the calibrating adapter are designed such that they can be replaced individually or together.

3. A gas sensor in accordance with claim 1, wherein the cap and the calibrating adapter are designed as a one-piece component.

4. A gas sensor in accordance with claim 1, wherein the cap consists essentially of PTFE (polytetrafluoroethylene) or hydrophobized PE (polyethylene).

5. A gas sensor in accordance with claim 1, wherein the cap comprises a sintered PTFE (polytetrafluoroethylene) or sintered hydrophobized PE (polyethylene) with a pore volume of about 30% to 70%.

6. A gas sensor in accordance with claim 1, wherein the gas sensor is an infrared optical gas sensor and the measuring element includes an infrared detector.

7. A gas sensor in accordance with claim 1, wherein the gas sensor is an electrochemical gas sensor and the measuring element is a measuring electrode.

8. A gas sensor in accordance with claim 1, wherein the gas sensor is a catalytic heat tone sensor and the measuring element is a pellistor.

9. A gas sensor in accordance with claim 1, wherein the cap is white.

10. A gas sensor in accordance with claim 1, wherein a porous, sintered metal body is arranged as an explosion protection means between said measuring element and said cap.

11. A gas sensor in accordance with claim 1, further comprising a cuvette heater in an area of the gas admission pipe connection of the calibrating adapter.

12. A gas sensor in accordance with claim 1, wherein said cap and said calibrating adapter are connected to the gas sensor both during the use for measurement and during the calibration.

13. A gas sensor in accordance with claim 1, wherein a flow resistance of the material of the cap is selected to be such that the pressure in the measuring cell exceeds the dynamic pressure of wind impinging on an outer side of said cap with the calibrating adapter during the calibration by means of calibrating gas fed in.

14. A gas sensor in accordance with claim 1, wherein due to the geometry of the calibrating adapter and the flow resistance of the material of the cap, the diffusion of measured gas to the measuring element is hindered only to the extent that the response time of the gas sensor during the gas measurement is prolonged by less than 30% compared to the operation without said calibrating adapter and said cap.

15. A gas sensor in accordance with claim 1, wherein a flow resistance of the material of the cap is selected to be such that the overpressure generated in the measuring cell by a calibrating gas flow through the gas admission pipe connection does not exceed 50 hPa.

16. A gas sensor, comprising:
   a measuring element, which generates a measured signal that depends on the concentration of a measured gas;
   a cap to delimit the gas sensor from the environment, the cap being made of a porous, gas-permeable and water-impermeable material; and
   a calibrating adapter having a gas admission pipe connection for supplying a calibrating gas to the cap of the gas sensor, said calibrating adapter being attached to or screwed on the cap, said cap having a smaller layer thickness and/or a higher porosity in an area of said gas admission pipe connection than in a remaining area.

17. A gas sensor, comprising:
   a measuring element, which generates a measured signal that depends on the concentration of a measured gas;
   a cylindrical cap to delimit the gas sensor from the environment, said cylindrical cap having a top wall and a side wall made of a porous, gas-permeable and water-impermeable material, whereby gas passes through said top wall in an axial direction and gas passes through said side wall in a radial direction, said top wall and said side wall having a surface exposed to the environment, said cap comprising a sintered PTFE (polytetrafluoroethylene) or sintered hydrophobized PE (polyethylene) with a pore volume of about 30% to 70%.

* * * * *